United States Patent [19]  [11] Patent Number: 4,917,668
Haindl  [45] Date of Patent: Apr. 17, 1990

[54] VALVE FOR PERMANENT VENOUS CANNULAE OR FOR CATHETER INSERTION MEANS

[75] Inventor: Hans-Guenter Haindl, Melsungen, Fed. Rep. of Germany

[73] Assignee: B.. Braun Melsungen AG, Melsungen, Fed. Rep. of Germany

[21] Appl. No.: 305,850

[22] Filed: Feb. 2, 1989

[30] Foreign Application Priority Data

Mar. 18, 1988 [DE] Fed. Rep. of Germany ....... 3809127

[51] Int. Cl.⁴ .............................................. A61M 5/18
[52] U.S. Cl. ..................................... 604/167; 604/169
[58] Field of Search ............... 604/167, 169, 237, 256, 604/905

[56] References Cited

U.S. PATENT DOCUMENTS 4,000,739 1/1977 Stevens ................................ 604/167
4,233,982 11/1980 Bauer et al. ...................... 604/169 X
4,243,034 1/1981 Brandt ................................. 604/169
4,496,348 1/1985 Genese et al. ...................... 604/167

Primary Examiner—John D. Yasko
Attorney, Agent, or Firm—Spensley Horn Jubas & Lubitz

[57] ABSTRACT

A housing having a channel is provided with a slotted, elastomeric valve body dividing the channel. The slotted valve body is biased in the closed position by a metal spring. If the valve body's material loses resiliency, the spring guarantees that the valve takes its closed position, even if the valve body is kept in the opened state for a considerable span of time by a steel cannula inserted through the valve body.

7 Claims, 3 Drawing Sheets

VALVE FOR PERMANENT VENOUS CANNULAE OR FOR CATHETER INSERTION MEANS

BACKGROUND OF THE INVENTION:

1. Field of the Invention

The present invention relates to a valve, and more particularly to a valve for permanent venous cannulae or for catheter insertion means.

2. Description of Related Art

To insert a venous catheter into a blood vessel, the vessel is first punctured with a permanent venous cannula. Such permanent venous cannulae typically consist of a steel cannula and plastic cannula slipped thereon. As soon as the puncture is made, the steel cannula is pulled out of the plastic cannula. The venous catheter can be inserted through the plastic cannula remaining in the vessel. It is also possible to leave the plastic cannula in the blood vessel for use as a short permanent catheter.

After the steel cannula has been pulled out of the plastic cannula, following a vessel puncture, blood may flow through the plastic cannula. Air may also enter the patient's body and air embolism may occur, if by an elevation of the thorax of the patient or by extreme desiccation of the patient the central venous pressure is negative.

In an attempt to avoid the risk of both an "air embolism" and a "blood contamination of the physician", German Patent 28 17 102 C2 discloses a valve integrated into the connection piece of a permanent venous cannula, which valve can only be opened in the direction toward the patient by mechanical action. A slotted Latex-disc serves as a valve body. In the delivery condition of the permanent venous cannula, the steel cannula is lead through the disc. After the puncture and the subsequent withdrawal of the steel cannula, the disc shuts itself due to its resilience. After that, a Luer connector can be set on the connection piece, which pushes open the disc with its conic pipe socket, so that the disc opens for the insertion of a venous catheter.

This known valve poses difficulties in storage, since it is stored with the steel cannula inserted through the disc. In the course of time, the elastomeric material of the disc loses its resilience, so that there is a danger that the valve will fail to close after a long storage. Thus, that part of the steel cannula that is enclosed by the elastic disc is made thinner than the rest of the cannula. Thus, the valve is spread open only negligibly during its storage. However, there is a danger that tissue particles and thrombi of the patient may settle at the constriction of the steel cannula, which could obstruct the constriction.

It is an object of the invention to provide a valve in which the valve shuts tightly, after the steel cannula has been pulled out and even after having been kept open for a long time.

SUMMARY OF THE INVENTION

In accordance with the present invention, this and other objectives are achieved by providing a spring, preferably of steel, in addition to the elastomeric valve body, which spring biases the valve body in the closing position. Contrary to elastomers, spring steel does not lose its resilient properties at all, or only to a much lesser extent, even during longer storage times. After pulling the steel cannula out of the valve, the additional spring safely pushes the valve body into the closing position, even after long storing.

In one embodiment of the invention, the spring may be provided as an axially resilient disc spring that is particularly simple, compact and cost effective.

In another embodiment of the invention, in order to open the valve body, the pipe connection of an external device acts directly on the collar of the disc extending from the patient.

In yet another embodiment of the invention, the channel is provided with a longitudinally displaceable sliding member that is biased by a separate spring (preferably of spring steel) toward the withdrawal position, in which is does not engage with the disc.

For keeping the valve body shut, another metal spring; e.g., a coil spring, may be used that is supported on the housing and presses against the opened disc with an axial component.

BRIEF DESCRIPTION OF THE DRAWINGS

A detailed description of various embodiments of the invention will be made with reference to the accompanying drawings, wherein like numerals designate corresponding parts in the several figures.

Figure 1:
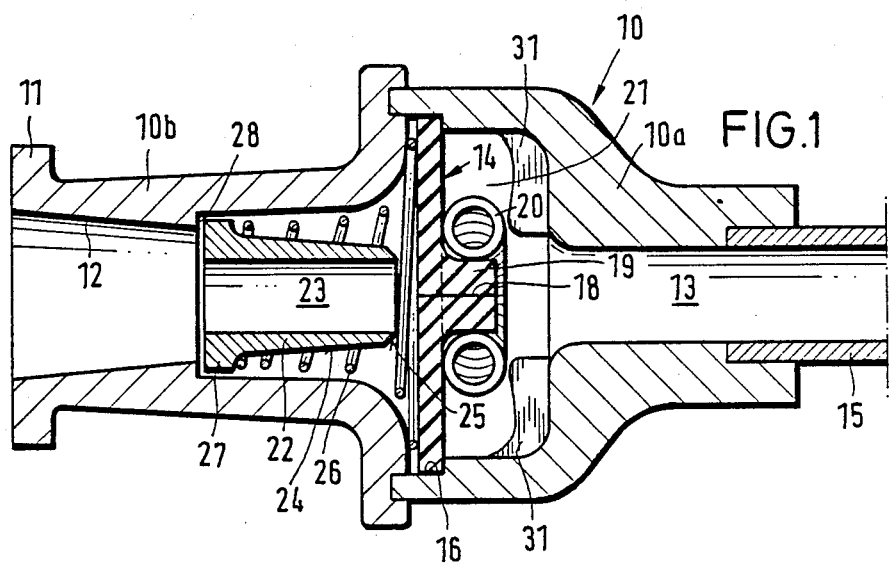
FIG. 1 shows a longitudinal section of an embodiment of the valve in the initial position.

DETAILED DESCRIPTION OF THE PREFERRED EMBODIMENTS:

The following detailed description is of the best presently contemplated mode of carrying out the invention. This description is not to be taken in a limiting sense, but is made merely for the purpose of illustrating the general principles of the invention. The scope of the invention is best defined by the appended claims.

The embodiment of the valve illustrated in FIGS. 1 to 4 has a two-piece longitudinal valve housing 10, having a housing part 10a directed toward the patient and a housing part 10b directed from the patient, which are firmly and tightly connected to each other. The housing part 10b is provided with connection elements 11 for a Luer-Lok-connector, the insertion opening 12 being provided as an inner core into which a pipe connection piece can be inserted.

The channel 13 extends longitudinally through the housing 10, the channel being longitudinally divided by the elastomeric valve body 14. The plastic cannula 15, which can be used either as an insertion aid for the catheter or directly as a short permanent catheter, protrudes from the end of the housing 10 that is directed toward the patient.

At its edge, the disc-shaped valve body 14 is fixed between the two parts of the housing 10a and 10b in a circumferential groove 16. As can be seen from FIG. 4, the valve body 14 has cross-shaped or Y-shaped slots, the slots being referred to as elements 17 and 18. The central part of the valve body 14 has a stud 19 or a nipple protruding toward the patient, into which the slots 17 and 18 also extend. Said stud 19 is surrounded by an annular spring 20 that biases the disc to the closed state in which the slots 17 and 18 are shut. A by-pass space 21 is provided in the housing part 10a behind the valve body 14, into which space the segments of the disc and the annular spring 20 can radially and axially evade when open.

A sliding member 22, having a longitudinally extending passage 23 and a conic outer surface 24, is disposed in the channel 13 in front of the valve body 14. The conic front end 25 of the sliding member 22 points to the central part of the valve body 14. The sliding member 22 is forced away from the valve body 14 by a metal coil spring 26 that presses against the flange 27 of the sliding member. The coil spring has a conic or a bell-shaped course and its enveloping surface is adapted to the inner surface of the housing part 10b. The larger end of the coil spring is fixed between the valve body 14 and the housing part 10b. To limit the initial position of the sliding member 22, an abutment 28 is provided in the housing part 10b.

FIG. 1 shows the valve in its initial position, in which the valve body 14 is closed and kept in the closed state by the annular spring 20. The sliding member 22 is in its withdrawal position.

Figure 2:
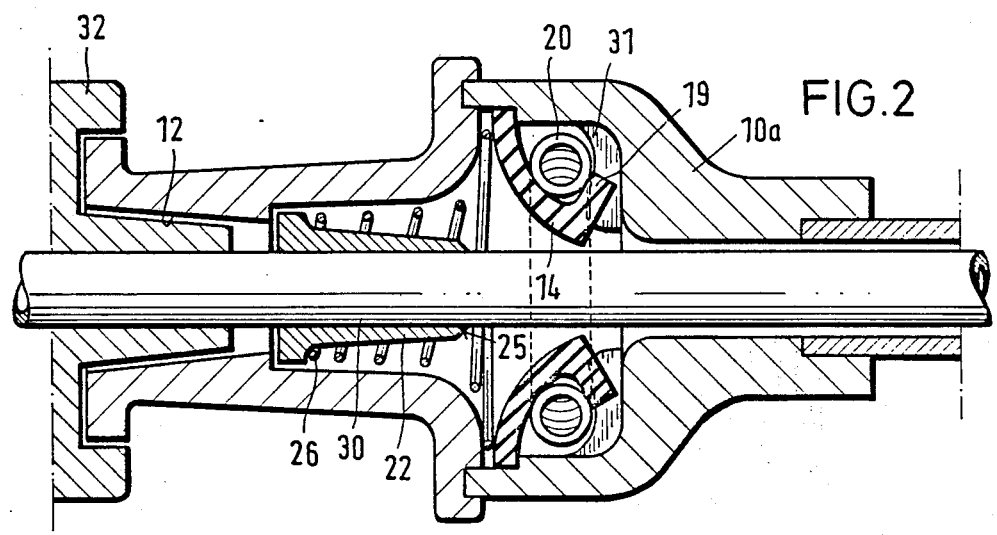
FIG. 2 shows a longitudinal section of an embodiment of the valve as delivered, with the steel cannula inserted.

FIG. 2 illustrates the valve with a steel cannula 30 inserted. The steel cannula 30 extends through the sliding member 22 without pulling the sliding member along. The steel cannula 30 opens the valve body 14, so that the segments of the valve body evade toward the end pointed toward the patient and so that the annular spring 20 is spread open.

The housing part 10a is provided with ribs 31 that extend into the gaps between the spread segments of the valve body 14 and that prevent the annular spring 20 from slipping axially off the stud 19. The ribs 31 provide longitudinal support for the annular spring 20 at the patient side, both in the relaxed state and in the biased state.

FIG. 2 illustrates the valve when stored having the steel cannula 30 in the channel 13, while a connector, through which the steel cannula passes, is fastened in the insertion opening 12. It is in this state that a blood vessel is punctured with the steel cannula, which is enclosed by the plastic cannula 15. If the steel cannula 30 is withdrawn subsequently, the valve body 14 closes under the effect of the annular spring 20, so that neither blood can flow from the housing 10, nor air enter into the plastic cannula 15.

Figure 3:
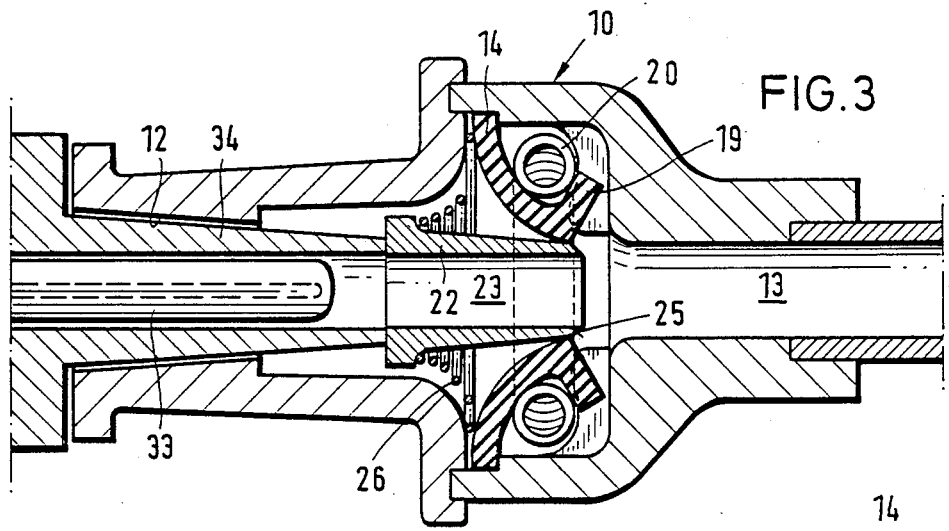
FIG. 3 shows a state of an embodiment of the valve after the steel cannula has been pulled out and during the insertion of a venous catheter.
Figure 4:
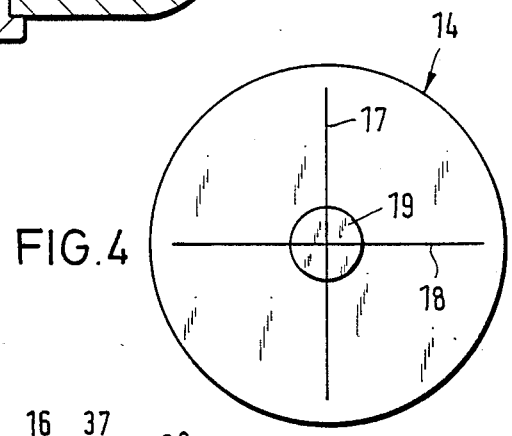
FIG. 4 shows a view of an embodiment of the elastomeric disc.

FIG. 3 shows the valve at insertion of a catheter 33 into the body through the opened valve and through the plastic cannula 15. The valve is opened by pushing the truncate-shaped pipe stud 34 of the insertion means from which the catheter 33 is advanced into the insertion opening 12. The pipe stud 34 is sufficiently long to press against the rear end of the sliding member 22 and to shift it forward, whereby the front end 25 of the sliding member opens the valve body, axially compressing the spring 26 at the same time. The inner diameter of the pipe stud 34 generally corresponds to the diameter of the channel 13 of the sliding member 22. Thus, the catheter 33 can be advanced within the sliding member 22 through the opened valve body 14. If the pipe stud 34 is subsequently withdrawn, the segments of the valve body 14 enclosed the catheter 33, since the sliding member 22 returns to its withdrawal position.

Figure 5:
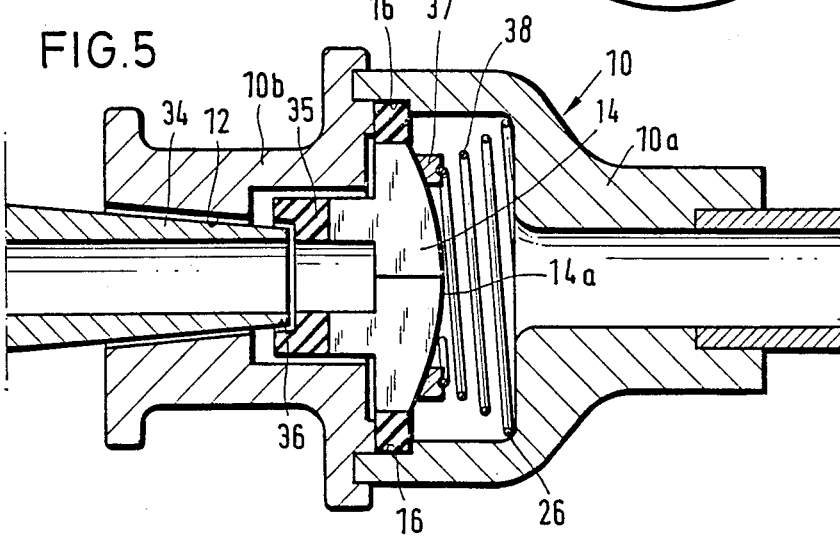
FIG. 5 shows a longitudinal section of a second embodiment of the valve, with the coil spring supported on the housing.

FIG. 5 illustrates an embodiment having no sliding member, shortly before the insertion of a catheter. The pipe stud 34 is in direct contact with an annular collar 35 formed integrally with the valve body 14, from which it extends backward. A corresponding groove 36 for taking up the front end of the pipe stud 34 is provided in the annular collar 35. When the pipe stud 34 is applied, it presses directly against the annular collar 35 of the valve body 14, so that an interposed sliding member is not required. The downstream end of the valve body 14 has a spherical outer surface 14a against which an adapter ring 37 is set. A truncated cone-shaped coil spring 38 acts on this adapter ring 37, which spring is supported on the housing 10 and which biases the segments of the valve body separated by the slots to the closed position. The adapter ring 37 engages with the perimeter of the segments of the valve body. When the valve body 14 is pushed open, the segments of the valve body slide to the adapter ring 37 and an opening that extends through the adapter ring 37, occurs in the valve body.

Figure 6:
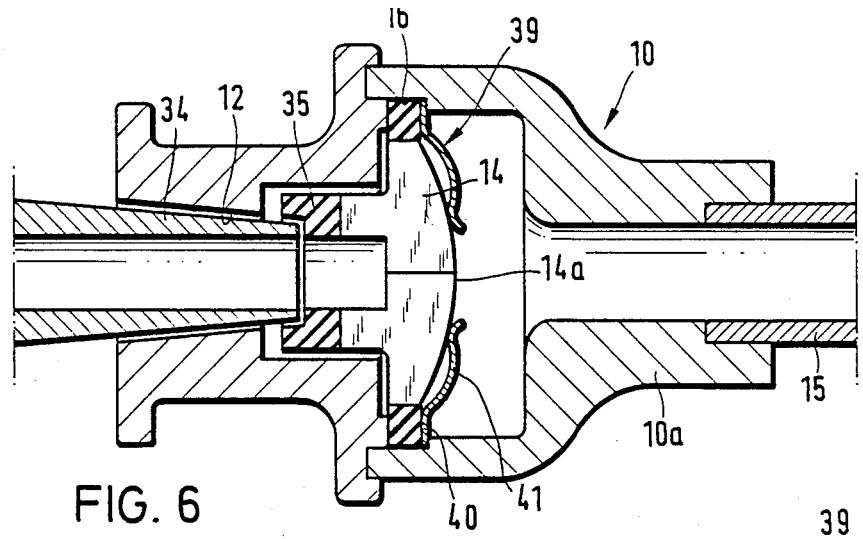
FIG. 6 shows an embodiment similar to the one in FIG. 5, but with a disc spring spanned together with the valve body.
Figure 7:
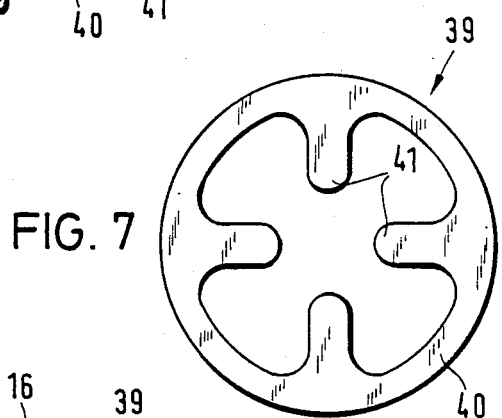
FIG. 7 shows a view of an embodiment of the disc spring and FIG. 8 shows a part illustration of the valve of FIG. 6 when open.
Figure 8:
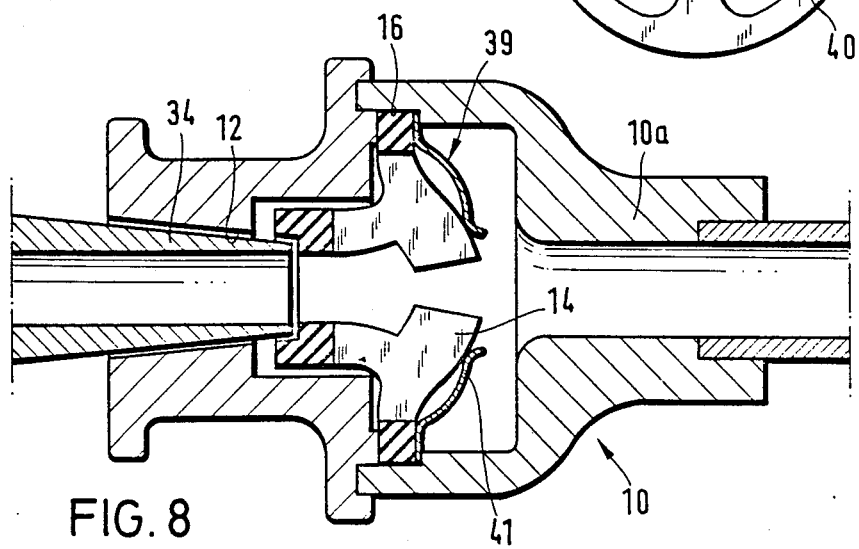

The valve body 14 of the embodiment in FIGS. 6 to 8 is provided in the same manner as in the embodiment in FIG. 5, but the spring is a plate spring 39 with a disc-shaped ring 40 from which the resilient arms 41 point radially inward. According to FIG. 6, the resilient arms 41 act on the spherical outer surface 14a of the valve body 14 and bias the valve body to the closed position.

FIG. 8 shows the opened state which is effected by the pipe stud 34 pushing open the valve body. The segments of the valve body 14 spread the resilient arms 41 of the disc spring 39. The ring 40 of the disc spring is fixed in the groove 16 of the housing 10 together with the outer edge of the valve body 14.

With the embodiments described above, the opening of the valve body 14 is always effected by an axial displacement of the pipe stud 34. It is also possible to provide the pipe stud 34 with a swivel nut that engages with threaded parts of the housing 10, so that the opened position of the valve can be adjusted by turning the swivel nut. Turning the swivel nut in the opposite direction may shut the valve body 14. To seal such a valve arrangement, it might be necessary to provide a seal ring between the insertion opening 12 and the pipe stud 34.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A valve for permanent venous cannulas or catheter insertion means, comprising:
   a housing having a longitudinally extending channel,
   an elastomeric valve body disposed in the channel and having a plurality of slots dividing the valve body into a plurality of segments, the valve body being alterable between a closed position in which the spacing between the segments is substantially minimized and an open position in which the spacing between the segments is relatively increased, insertion means for pushing the valve body into the open position, and a spring for biasing the valve body in the closed position.

2. The valve according to claim 1, wherein the spring is a disc spring having inwardly directed arms for pressing against the valve body.

3. The valve according to claim 1, wherein the insertion means further comprises means for inserting a pipe stud for pushing the valve body into the open position and wherein the valve body further comprises an annular collar configured for receiving the pipe stud.

4. The valve according to claim 1, wherein the valve body further comprises a stud extending axially from the center of the valve body and being divided into a plurality of segments by the slots, and wherein the spring is disposed to radially compress the segments of the stud.

5. The valve according to claim 1, further comprising:

a longitudinally displaceable sliding member having an end configured to be pressed against the central part of the valve body, and a biasing spring for biasing the sliding member away from the valve body.

6. The valve according to claim 1, wherein the housing is provided with an escape space into which the segments of the valve body spread in the open position, and further comprising a plurality of ribs, protruding into the space and extending between the segments of the valve body, for preventing slippage of the spring.

7. The valve according to claim 1, wherein the spring is a coil spring supported on the housing and further comprising an adapter member pressed by the spring against the valve body.

* * * * *